United States Patent [19]
Ives

[11] Patent Number: 5,275,172
[45] Date of Patent: Jan. 4, 1994

[54] ELECTROENCEPHALOGRAPHIC SIGNAL ACQUISITION AND PROCESSING SYSTEM

[75] Inventor: John R. Ives, Lexington, Mass.

[73] Assignee: Beth Israel Hospital Association, Boston, Mass.

[21] Appl. No.: 871,307

[22] Filed: Apr. 20, 1992

[51] Int. Cl.⁵ .......................................... A61B 5/0476
[52] U.S. Cl. .................................................. 128/731
[58] Field of Search ...................................... 128/731-; 364/413.02, 413.05

[56] References Cited

U.S. PATENT DOCUMENTS

| | | | |
|---|---|---|---|
| 3,896,790 | 7/1975 | Dikmen | 128/732 X |
| 4,092,981 | 6/1978 | Ertl | 128/731 |
| 4,610,259 | 9/1986 | Cohen et al. | 128/731 |
| 4,800,895 | 1/1989 | Moberg et al. | 128/731 |

Primary Examiner—Angela D. Sykes
Attorney, Agent, or Firm—Reed Smith Shaw & McClay

[57] ABSTRACT

A system for remontaging EEG signals includes acquiring a first set of bipolar signals in a first montage defined by the locations of electrodes on a patient, synthesizing a second set of bipolar signals corresponding to a second montage defined by the electrode locations, and displaying, printing, or recording the second set of signals. Preferably, the first set of bipolar signals is converted to a set of monopolar signals, from which bipolar signals corresponding to any desired montage defined by the electrode location may be synthesized. This system permits remontaging of signals without the drawbacks of existing remontaging systems, which use monopolar signal acquisition.

29 Claims, 4 Drawing Sheets

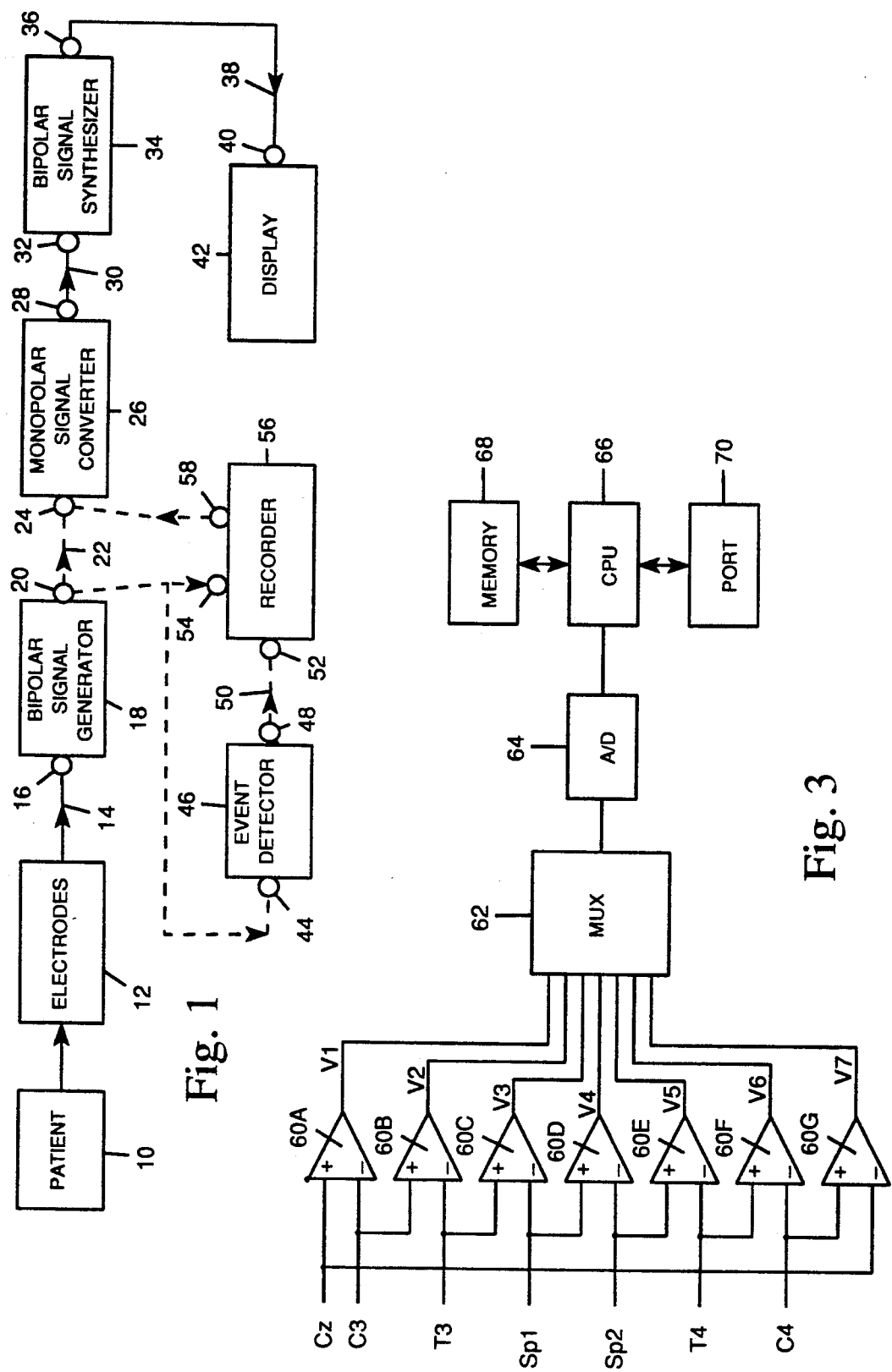

ELECTROENCEPHALOGRAPHIC SIGNAL ACQUISITION AND PROCESSING SYSTEM

FIELD OF THE INVENTION

This invention relates to neurological monitoring, particularly electroencephalographic (EEG) monitoring. More particularly, this invention relates to a method and apparatus for acquiring, recording, computing, and displaying EEG signals.

BACKGROUND OF THE INVENTION

Two basic techniques have been used for recording and displaying EEG signals. Such signals are obtained from electrodes coupled to the head of a patient being monitored. Electrodes are located on a patient and signals are obtained from the electrodes in a pattern known as a "montage". In the first method, "bipolar" recording, differential signals are obtained from and recorded between pairs of electrodes which are generally adjacent, and each electrode may be used in more than one such differential measurement. Bipolar signals are typically acquired in a chain-like array, with differential signals being obtained between first and second electrodes, second and third electrodes, third and fourth electrodes, and so forth. In the second method, "monopolar" or "referential" recording, one of the electrodes is used as a reference electrode for all signals, and signals are obtained and recorded from each of the other electrodes with respect to the reference electrode.

Bipolar recording has the advantage of providing relatively high quality signals, since the signal between adjacent electrodes has a relatively small spurious noise signal component and the differential signal obtained is in principle unaffected by common mode signals. However, in the past a bipolar signal could be displayed only for the electrode montage in which it was acquired and recorded.

Monopolar recording has provided the ability to "remontage" the recorded signals, i.e. to compute and display EEG signals corresponding to any bipolar montage which may be defined by the locations of the electrodes, to simulate the signals which would have been recorded if bipolar signals were obtained from the electrodes. The monopolar method has several disadvantages. First, the monopolar recording is entirely dependent on the integrity of the reference electrode. This is particularly troublesome in unattended ambulatory monitoring, where patient movement increases the likelihood that an electrode may become detached, and an entire recording session may be compromised by loss of electrode integrity. Second, monopolar signals include relatively high common-mode signals. This necessitates expensive, high-precision amplifiers to obtain signals which are suitable for remontaging, and such amplifiers tend to be high powered devices which limits their use in battery-operated recording such as ambulatory monitoring. The high common-mode signal components also substantially impact other aspects of the signal processing required. While 8 bit digitization is generally acceptable in bipolar recording, even 12 bits may not provide sufficient dynamic range to properly record a monopolar signal during a seizure. If an EEG signal hits a power supply rail and is clipped, a remontaged signal will not be valid. The extra dynamic signal range of monopolar recording requires more expensive and precise electronics, greater speed, and greater recording capacity for a given monitoring period. Third, monopolar acquisition and recording substantially impedes analysis of EEG signals. Raw monopolar signals cannot be directly read by an electroencephalographer, particularly during a seizure when all channels contain what appears to be significant generalized activity. Moreover, existing algorithms for automatic detection of seizures and other events do not work with monopolar signals. Thus, to enable automatic event detection in monopolar recording, either such algorithms must be rewritten or the monopolar signals must be converted "on the fly" to bipolar signals prior to applying a conventional algorithm.

SUMMARY OF THE INVENTION

It is therefore a general object of the invention to provide an EEG signal acquisition, recording, and processing system which provides the advantages of both bipolar and monopolar recording without the disadvantages of either. The present invention includes acquiring and recording a first set of bipolar signals in a first montage defined by the electrode locations, synthesizing a second set of signals representing the signals which would have been acquired in a second montage defined by the electrode locations, and storing or displaying the second set of signals. Other objects and features of the invention will appear upon review of the following specification and claims and the drawings.

BRIEF DESCRIPTION OF THE DRAWINGS

FIG. 1 is a general block diagram of an EEG system in accordance with the present invention.

FIG. 3 is a block diagram of preferred apparatus for implementing the functions illustrated in FIGS. 1 and 2.

DETAILED DESCRIPTION

Figures 2, 2A, 2B:
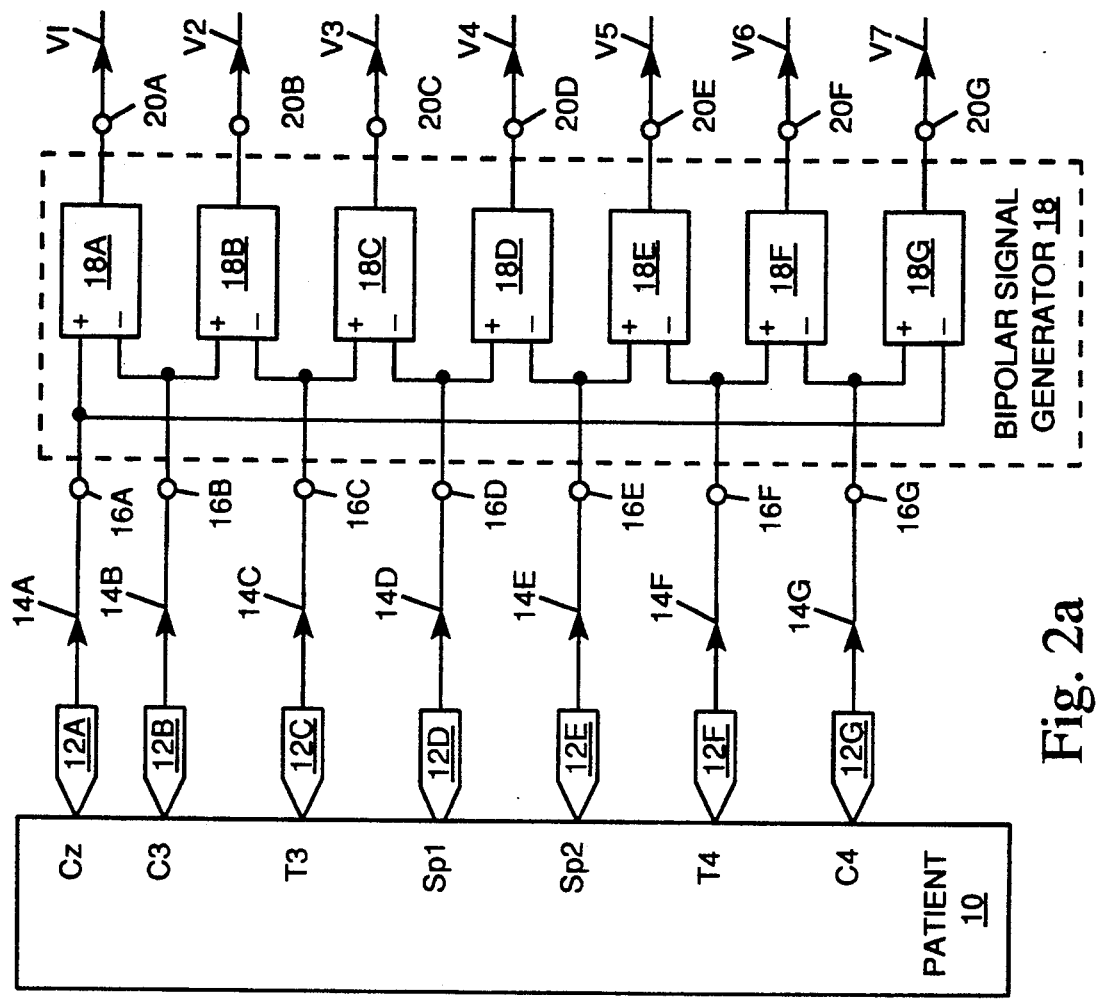
FIG. 2, consisting of FIGS. 2a and 2b, is a more detailed general block diagram of an EEG system in accordance with the present invention.
Figure 2B:
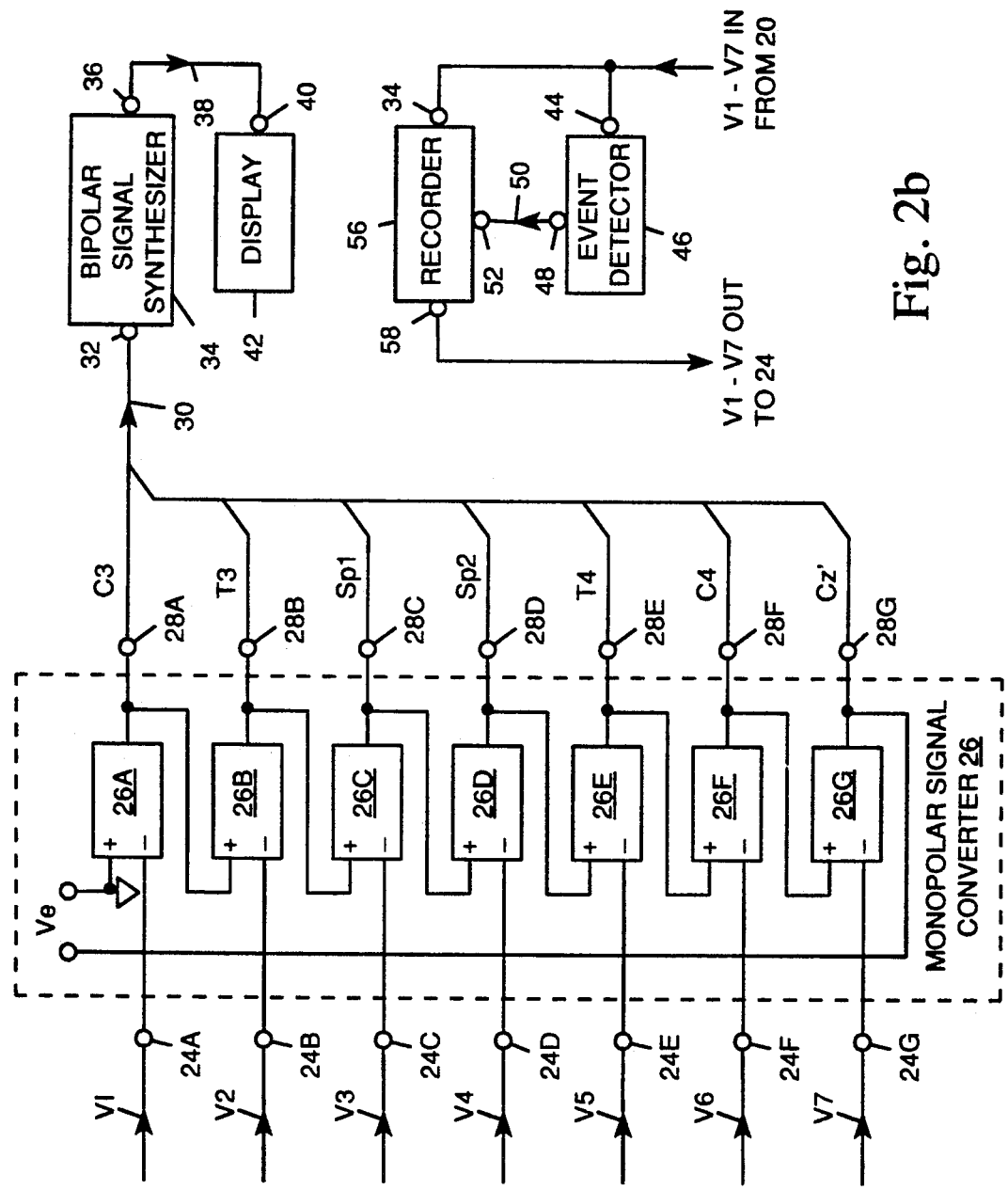

FIG. 1 is a general block diagram illustrating the EEG signal acquisition and processing system of the present invention. A plurality of electrodes 12 is coupled to a patient 10 to be monitored. The electrode signals 14 produced by the electrodes are supplied to the input 16 of a bipolar signal generator 18, which produces bipolar signals 22 at an output 20 corresponding to a first montage defined by the locations of electrodes 12 on patient 10. The acquired bipolar signals 22 are supplied to the input 24 of a monopolar signal converter 26, which produces monopolar signals 30 at its output 28. The monopolar signals 30 correspond to the signals present, with respect to one of the electrodes 12 selected as a reference, at each of the other electrodes 12. The derived monopolar signals 30 are supplied to the input 32 of bipolar signal synthesizer 34, which synthesizes bipolar signals at its output 36 corresponding to any desired montage which may be defined by the locations of the electrodes 12 on patient 10. The synthesized bipolar signals 38 may be supplied to the input 40 of a display 42 for display to an electroencephalographer, or they may be recorded.

In order to preserve monitoring results for later display, analysis, or documentation of patient condition, a recorder 56 may be provided. Preferably the acquired bipolar signals 22 are supplied to a recording input 54 of recorder 56, and recorded signals may thereafter be supplied from the recorder output 58 to monopolar signal converter 26 and synthesizer 34 to generate desired bipolar signals. If desired, the converted monopolar signals 30 or synthesized bipolar signals 38 may be recorded instead of or in addition to the acquired bipolar signals.

In many applications it is desirable to record signals primarily when neurologically significant events are occurring. This reduces the amount of data which must be analyzed and, of particular significance in unattended ambulatory recording, it reduces the amount of data which must be stored. In accordance with an important aspect of the invention, acquired bipolar signals 22 are available to be supplied to an input 44 of an event detector 46. Event detector 46 may operate on the acquired bipolar signals 22 using available and conventional seizure and spike detection techniques to produce an event signal 50 at output 48 upon detection of an event. The event signal 50 may be supplied to a control input 52 of recorder 56 to control its recording operations.

FIG. 2 is a more detailed block diagram illustrating the functions performed by the system of the present invention, in which elements which correspond to elements in FIG. 1 are indicated by the same reference numerals. A plurality of electrodes 12 is coupled to the head of a patient 10 at locations from which neurological signals are desired. In the example shown, seven electrodes 12A, 12B, . . . 12G are used; these are coupled to the patient 10 at locations Cz, C3, T1, Sp1, Sp2, T4, and C4, respectively. It will be understood that the number and location of the electrodes is a matter of choice and the invention is not limited to the electrode number and location set forth in the illustrated example.

The neurological signals 14 present on electrodes 12 are coupled to the inputs 16 of bipolar signal generator 18 which produces outputs 20 which are responsive to the differences between selected pairs of inputs. As illustrated, bipolar signal generator 18 includes inputs 16A–16G each of which is coupled to one of the electrodes 12A–12G, and produces outputs 20A–20G having signals 22 which respond to differences between electrode signals 14A–14G present at inputs 16. The outputs 20A–20G contain signals 22, comprising signals V1–V7, as follows:

$$\begin{aligned}
V1 &= Cz - C3 \\
V2 &= C3 - T3 \\
V3 &= T3 - Sp1 \\
V4 &= Sp1 - Sp2 \\
V5 &= Sp2 - T4 \\
V6 &= T4 - C4 \\
V7 &= C4 - Cz
\end{aligned}$$

It will be understood that the signals V1–V7 may be proportional to or otherwise related to the differences between the input signals 14, rather than equal to the differences as indicated. The differential signals V1–V7 are conventional bipolar EEG signals. These signals 22 may be supplied to an event detecting device 46 such as by digitizing the signals and supplying them to a computer which operates conventional seizure and spike detection software. An event output signal 50 of event detecting device 46 may be used to control operation of a recording device 56, for instance to record EEG signals during detected seizure or spike events.

Further processing of the acquired bipolar signals differs from conventional bipolar monitoring. The bipolar signals V1–V7 are supplied to signal processing elements which produce output signals corresponding to other montages than the one in which the signals V1–V7 were acquired.

In the preferred embodiment of FIG. 2, the acquired bipolar signals are converted to monopolar signals with respect to the signal present on a selected reference electrode. Bipolar signals V1–V7 are supplied to inputs 24A–24G of monopolar signal converter 26. Monopolar signal converter 26 includes means 26A–26G for subtracting various combinations of the signals V1–V7 to produce monopolar output signals 30 at monopolar signal converter outputs 28A–28G. In the example of FIG. 2, the outputs 30 include monopolar signals C3, T3, Sp1, Sp2, T4 and C4 with respect to the signal Cz selected as a reference. Cz is selected as the reference by setting an input to subtracting means 26A to zero, and the monopolar value of the remaining signals is calculated with respect to Cz as follows:

$$\begin{aligned}
Cz &= 0 \\
C3 &= Cz - V1 = -V1 \\
T3 &= C3 - V2 = -V1 - V2 \\
Sp1 &= T3 - V3 = -V1 - V2 - V3 \\
Sp2 &= Sp1 - V4 = -V1 - V2 - V3 - V4 \\
T4 &= Sp2 - V5 = -V1 - V2 - V3 - V4 - V5 \\
C4 &= T4 - V6 = -V1 - V2 - V3 - V4 - V5 - V6.
\end{aligned}$$

The system of FIG. 2 includes means for checking the accumulation of errors in the calculations. A further subtraction is effected by subtracting means 26G to provide an error signal Cz', as follows:

$$Cz' = C4 - V7 = -V1 - V2 - V3 - V4 - V5 - V6 - V7.$$

Cz' is ideally equal to zero, the value assigned to Cz in the calculation. The value of Cz' indicates the extent of errors Ve in the calculations, and may be recorded, displayed, or compared with a reference value to provide an output indicating whether the results should be deemed valid or invalid.

Other electrodes may be selected as the reference by appropriate input of a zero to the subtraction means.

The monopolar signals 30 are supplied to the input 32 of a bipolar signal synthesizer 34 which produces output signals 38 at output 36 corresponding to any desired montage which may be defined by the locations of electrodes 12 on patient 10. The bipolar synthesis may be effected by subtracting selected pairs of the monopolar signal values Cz, C3, T3, Sp1, Sp2, T4, and C4 corresponding to the desired montage. The synthesized bipolar output signals may be supplied to the input 40 of a display 42.

While any of the signals in the system may be recorded, it is believed preferable to record the acquired bipolar signals 22. Accordingly, instead of or in addition to being supplied to monopolar signal converter 26, the acquired bipolar signals 22 are supplied to a recording input 54 of recorder 50. Recorded bipolar signals may later be supplied from recording output 58 to input 24 of monopolar signal converter 26 and then to synthesizer 34 for synthesis and display of desired bipolar signals. Because bipolar signals V1–V7 are present in the system of FIG. 2, they may be supplied to input 44 of event detector 46 which detects neurologically significant events such as seizures and spikes by conventional methods. Upon the occurrence of such an event, an event output signal 50 is generated at output 48 and supplied to recorder control input 52 to provide recording of neurological signals related to the event. This feature is especially advantageous in unattended ambulatory EEG monitoring, where it is important to minimize the amount of data which must be recorded while still obtaining useful EEG information.

Having described the functions of the system of FIG. 2, it is noted that they may be implemented by a wide variety of apparatus, which may provide analog and/or digital signals at various portions of the apparatus. For instance, the bipolar signal generator 18 will typically comprise a plurality of analog differential amplifiers to amplify the low level EEG signals present at the electrodes 12. All further signal processing may likewise be analog. Monopolar signal generator 26 may comprise a plurality of analog differential amplifiers, recorder 50 may be an analog recording device such as a tape recorder, and bipolar signal synthesizer 34 may comprise a plurality of differential amplifiers. It is believed preferable, however, for at least part of the signal processing to be performed digitally, and for signal recording to be performed digitally. Moreover, it may be preferable to perform the signal processing in bipolar signal generator 18, monopolar signal converter 26, and/or bipolar signal synthesizer 34 by multiplexing the signals and operating on the multiplexed signals with a single processing element.

FIG. 3 is a block diagram of a particularly preferred embodiment of the system of the invention which includes initial analog processing and subsequent digital processing. The electrode signals Cz-C4 are coupled to pairs of inputs of amplifier array 60 comprising amplifiers 60A-60G. These provide amplified differential signals V1-V7 corresponding to the signals between pairs of electrodes. These bipolar signals are supplied to inputs of multiplexer 62, which multiplexes them and supplies the multiplexed signals to analog-to-digital (A/D) converter 64 which digitizes them. The digitized signals are supplied to a computer system including central processing unit (CPU) 66, memory 68, and port 70. Memory 68 includes a stored operating program for execution by CPU 66. CPU 66, under control of the operating program, provides the monopolar signal conversion and bipolar signal synthesis functions corresponding to blocks 26 and 34 of FIG. 1. CPU 66 may also provide the event detector function of block 46 of FIG. 1, operating on bipolar input signals in accordance with event detection algorithms stored in memory 68. Digitized bipolar signals may be stored in memory 68, which preferably contains digital solid state memory to perform this function but may utilize other means such a disk or tape storage. Thus, memory 68 may implement the function of recorder 56 illustrated in FIGS. 1 and 2. Desirably, memory 68 is large enough to store all operating programs as well as all data which may be desired to be stored in a neurological monitoring procedure. In that event, CPU 66 may synthesize the desired bipolar signals and output them via port 70 to a display device such as a monitor or printer. Alternatively, the functions described for CPU 66 and memory 68 may be performed by separate processors and memories. For instance, ambulatory monitoring may involve a portable, patient-worn apparatus which stores acquired bipolar signals in a memory 68 under control of a CPU 66, and the stored signals may later be output via port 70 to a stationary computer system such as in a neurologist's office for archiving of data, any necessary further signal processing such as monopolar conversion and bipolar synthesis, display, printing, and analysis.

Figure 4:
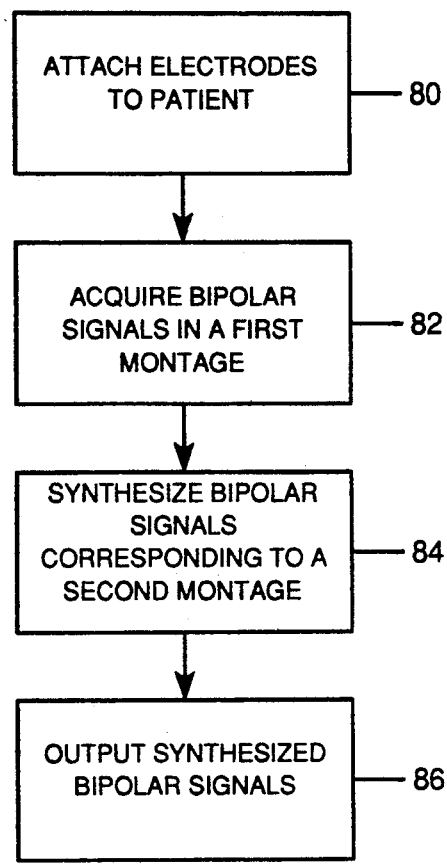
FIG. 4 is a general flow diagram of a method of remontaging in accordance with the present invention.

FIG. 4 is a general flow diagram of the remontaging method of the present invention. A plurality of electrodes is attached to a patient in step 80, in locations on the patient where physiological signals of interest will occur. In step 82, bipolar signals are acquired in a first montage defined by the locations of the electrodes on the patient. In step 84, bipolar signals corresponding to a second montage defined by the electrode locations are synthesized based upon the acquired bipolar signals. In step 86, the synthesized bipolar signals corresponding to the second montage are output, such as to a display device or storage device.

FIG. 4 illustrates that in general, it is not necessary to perform an intermediate signal conversion step between the bipolar signal acquisition step and the bipolar signal synthesis step. That is, a desired second set of bipolar signals can be synthesized directly from the acquired bipolar signals. Although applicants prefer to use an intermediate conversion to monopolar signals, it should be further understood that any intermediate conversion step may provide bipolar intermediate signals rather than monopolar intermediate signals.

Figure 5:
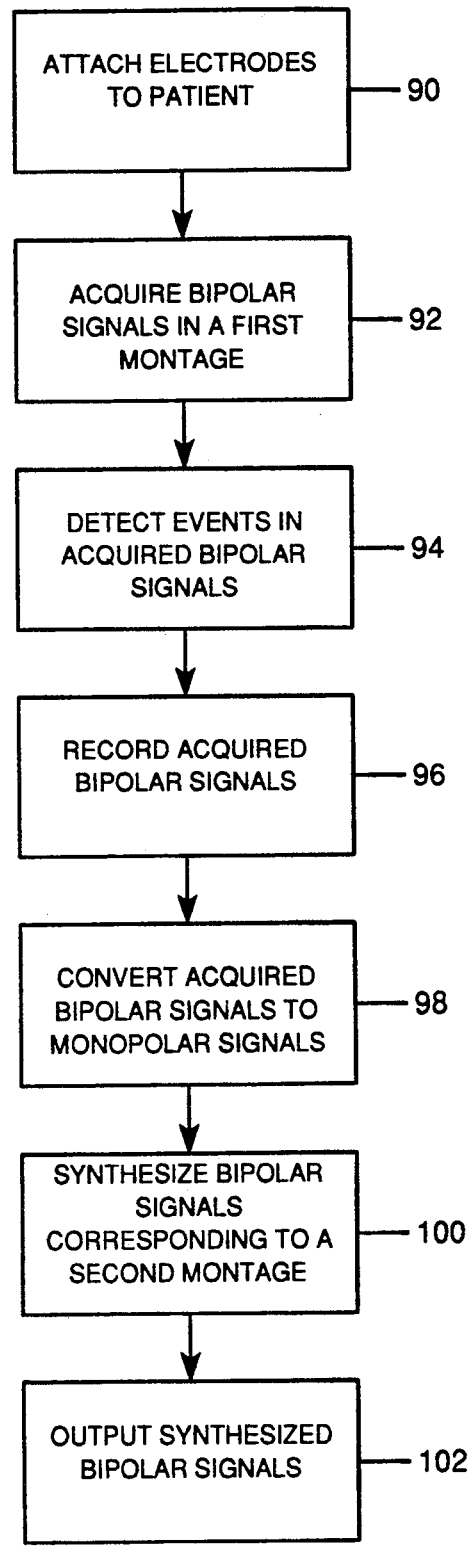
FIG. 5 is a more specific flow diagram of a preferred method of remontaging in accordance with the present invention.

FIG. 5 is a more specific flow diagram illustrating the preferred remontaging method of the invention. A plurality of electrodes is attached to a patient in step 90, in locations on the patient where physiological signals of interest will occur. In step 92, bipolar signals are acquired in a first montage defined by the locations of the electrodes on the patient. In step 94, events of potential neurological significance such as seizures and spikes are detected in the acquired bipolar signals, and the recording step 96 is controlled at least in part in response to the results of the event detecting step. In step 98, the acquired bipolar signals are converted to monopolar signals. In step 100, bipolar signals corresponding to a second montage defined by the electrode locations are synthesized based upon the monopolar signals, and the synthesized bipolar signals are output in step 102 such as to a display device or a storage device.

While particular embodiments of the invention have been described, others will no doubt occur to those skilled in the art without departing from the spirit and scope of the invention.

What is claimed is:

1. A method of providing electroencephalographic signals comprising the steps of:
   coupling a plurality of electrodes to a patient;
   acquiring a set of bipolar signals from said electrodes in a first montage defined by the locations of said electrodes; and
   synthesizing a set of bipolar signals based upon said acquired set of bipolar signals, said synthesized set of bipolar signals corresponding to signals occurring at said electrodes in a second montage defined by the location of said electrodes.

2. A method according to claim 1, further comprising the step of recording a set of said signals.

3. A method according to claim 2, wherein said recording step includes recording said acquired set of bipolar signals.

4. A method according to claim 1, further comprising the step of detecting neurologically significant events in said acquired set of bipolar signals.

5. A method according to claim 4, further comprising the step of recording a set of said signals in response to the results of said detecting step.

6. A method according to claim 1, further comprising the step of converting said acquired set of bipolar signals to a set of intermediate signals, wherein said second set of bipolar signals is synthesized from said intermediate set of signals.

7. A method according to claim 6 wherein said intermediate signals are monopolar signals.

8. A method according to claim 1, further comprising the step of outputting said synthesized set of bipolar signals to a device selected from the group consisting of display, printing, and recording devices.

9. An electroencephalographic system comprising:
a plurality of electrodes adapted to be coupled to a patient in locations on the patient to provide electrode signals;
a bipolar signal generator coupled to said electrodes and generating a set of acquired bipolar signals in a first montage defined by the locations of said electrodes on said patient; and
a bipolar signal synthesizer coupled to said bipolar signal generator, said bipolar signal synthesizer producing a set of synthesized bipolar signals based upon said acquired bipolar signals, said synthesized bipolar signals corresponding to signals occurring at said electrodes in a second montage defined by said electrode locations.

10. A system according to claim 9, including a recorder receiving and recording signals responsive to said electrode signals.

11. A system according to claim 10, wherein said received and recorded signals include acquired bipolar signals.

12. A system according to claim 10, wherein said recorder includes digital solid state memory.

13. A system according to claim 10, including an event detector receiving said acquired bipolar signals and producing an event signal upon the occurrence of a neurologically significant event in said acquired bipolar signals.

14. A system according to claim 13, including a recorder receiving said event signal and recording signals responsive to said electrode signals upon receipt of said event signal.

15. A system according to claim 13, wherein said event detector detects events selected from the group consisting of seizure events and spike events in said acquired bipolar signals.

16. A system according to claim 9, including an intermediate signal processor, said bipolar signal synthesizer being coupled to said bipolar signal generator by said intermediate signal processor.

17. A system according to claim 16, wherein said intermediate signal processor converts said acquired bipolar signals to monopolar signals.

18. A system according to claim 9, further including a device selected from the group consisting of display and storage devices coupled to said bipolar signal synthesizer for receiving said synthesized bipolar signals.

19. A system according to claim 9, further including an analog-to-digital converter coupled to said bipolar signal generator and producing digital signals responsive to said acquired bipolar signals.

20. A system according to claim 19, further including a central processing unit receiving said digital signals produced by said analog-to-digital converter.

21. A system according to claim 20, wherein said central processing unit comprises a monopolar signal converter.

22. A system according to claim 19, wherein said bipolar signal synthesizer includes a central processing unit.

23. An electroencephalographic system comprising:
means for acquiring a set of, bipolar signals from electrodes adapted to be coupled to a patient in predetermined locations, said set of bipolar signals being acquired in a first montage defined by the electrode locations; and
means for synthesizing a set of bipolar signals from said acquired bipolar signals, said synthesized bipolar signals corresponding to signals occurring in a second montage defined by the electrode locations.

24. A system according to claim 23, further including means for recording signals responsive to said acquired bipolar signals.

25. A system according to claim 24, wherein said recording means includes digital solid state memory.

26. A system according to claim 23, further including means for detecting neurologically significant events in said acquired bipolar signals.

27. A system according to claim 26, wherein said event detecting means includes means for detecting events selected from the group consisting of seizure events and spike events in said acquired bipolar signals.

28. A system according to claim 23, further including means for converting said acquired bipolar signals to monopolar signals.

29. A system according to claim 23, further including display means for displaying said synthesized bipolar signals.

* * * * *